(12) United States Patent
Lai

(10) Patent No.: US 10,905,157 B2
(45) Date of Patent: Feb. 2, 2021

(54) ELECTRONIC CIGARETTE AND ATOMIZING DEVICE THEREOF

(71) Applicant: SHENZHEN SMOORE TECHNOLOGY LIMITED, Shenzhen (CN)

(72) Inventor: Baosheng Lai, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 329 days.

(21) Appl. No.: 16/131,039

(22) Filed: Sep. 14, 2018

(65) Prior Publication Data
US 2019/0223497 A1    Jul. 25, 2019

(30) Foreign Application Priority Data
Jan. 24, 2018 (CN) .................... 2018 2 0123428 U

(51) Int. Cl.
*A24F 40/48* (2020.01)
*A24F 15/015* (2020.01)
*A24F 47/00* (2020.01)

(52) U.S. Cl.
CPC ............ *A24F 15/015* (2020.01); *A24F 40/48* (2020.01); *A24F 47/008* (2013.01)

(58) Field of Classification Search
None
See application file for complete search history.

(56) References Cited

U.S. PATENT DOCUMENTS

| | | | |
|---|---|---|---|
| 2016/0095356 A1* | 4/2016 | Chan | H05B 3/44 131/329 |
| 2016/0219934 A1* | 8/2016 | Li | B65D 85/70 |
| 2016/0219935 A1* | 8/2016 | Qiu | A24F 47/008 |
| 2016/0249683 A1* | 9/2016 | Li | A24F 47/008 131/329 |
| 2017/0202268 A1* | 7/2017 | Li | F16J 15/022 |
| 2018/0035718 A1* | 2/2018 | Liu | A24F 47/00 |
| 2018/0153220 A1* | 6/2018 | Verleur | A24F 40/40 |
| 2018/0160738 A1* | 6/2018 | Verleur | A61M 15/06 |
| 2018/0271148 A1* | 9/2018 | Liu | A24F 40/48 |
| 2018/0352865 A1* | 12/2018 | Qiu | A24F 15/015 |

(Continued)

*Primary Examiner* — James Harvey
(74) *Attorney, Agent, or Firm* — Hemisphere Law, PLLC; Zhigang Ma

(57) ABSTRACT

The present disclosure provides an atomizing device, including a liquid reserving assembly and a cigarette holder assembly rotatably mounted at one end of the liquid reserving assembly. A liquid storage cavity is formed inside the liquid reserving assembly, and a liquid inlet is arranged at one end of the liquid reserving assembly corresponding to the cigarette holder assembly. The cigarette holder assembly includes an axially-penetrating smoke outlet, the liquid reserving assembly includes a smoke passage correspondingly communicating with the smoke outlet, and the cigarette holder assembly blocks the liquid inlet. The cigarette holder assembly includes a positioning member axially movable between a first position and a second position; when being in the first position, the positioning member is engaged with the liquid reserving assembly, and the cigarette holder assembly blocks the liquid inlet; and when being in the second position, the positioning member is separated from the liquid reserving assembly.

20 Claims, 6 Drawing Sheets

(56) References Cited

U.S. PATENT DOCUMENTS

2019/0307174 A1* 10/2019 Qiu ..................... A24F 47/008
2020/0164165 A1* 5/2020 Lord .................... A61M 11/042
2020/0221776 A1* 7/2020 Liu ....................... A24F 40/44

* cited by examiner

ELECTRONIC CIGARETTE AND ATOMIZING DEVICE THEREOF

TECHNICAL FIELD

The present disclosure generally relates to substitutes for tobacco cigarettes, and more particularly, to an electronic cigarette and an atomizing device thereof.

BACKGROUND

In general, a reusable electronic cigarette can continue to be used by re-injecting tobacco liquid into a cartridge after the tobacco liquid is exhausted. However, during the process of injecting the tobacco liquid, a mouthpiece of the electronic cigarette usually needs to be removed before the tobacco liquid is injected into the cartridge, which is cumbersome. Moreover, the removed cigarette holder may easily drop off or get lost, which is very inconvenient.

There is also a rotary connection between the mouthpiece and the cartridge. When the mouthpiece is rotated, a liquid inlet on the cartridge is opened to facilitate liquid injection. However, the rotational connection of the cigarette holder is likely to cause rotation or misrotation during use, which may cause a risk of liquid leakage.

Technical Problem

Therefore, the present disclosure aims to provide an improved electronic cigarette and an atomizer thereof for preventing accidental opening of a liquid inlet.

SUMMARY OF THE DISCLOSURE

An atomizing device provided in the present disclosure includes a liquid reserving assembly and a cigarette holder assembly rotatably mounted at one end of the liquid reserving assembly; a liquid storage cavity is formed inside the liquid reserving assembly, and a liquid inlet for injecting liquid into the liquid storage cavity is arranged at one end of the liquid reserving assembly corresponding to the cigarette holder assembly; the cigarette holder assembly includes an axially-penetrating smoke outlet, the liquid reserving assembly includes a smoke passage correspondingly communicating with the smoke outlet; the cigarette holder assembly blocks the liquid inlet; a rotation axis of the cigarette holder assembly is offset from the liquid inlet to expose the liquid inlet after rotation; the cigarette holder assembly includes a positioning member axially movable between a first position and a second position, when being in the first position, the positioning member is engaged with the liquid reserving assembly to limit the cigarette holder assembly to rotating relative to the liquid reserving assembly, and the cigarette holder assembly blocks the liquid inlet; and when being in the second position, the positioning member is separated from the liquid reserving assembly, so that the cigarette holder assembly rotates relative to the liquid reserving assembly to expose the liquid inlet.

In an embodiment, the cigarette holder assembly further includes an elastic member that provides an elastic force for holding the positioning member in the first position.

In an embodiment, the positioning member includes an annular sleeve portion, one end of the sleeve portion is sleeved at the end of the liquid reserving assembly corresponding to the cigarette holder assembly; and an annular clamping table corresponding to a shape of an inner ring of the sleeve portion is arranged at one end of the liquid reserving assembly corresponding to the sleeve portion for the sleeve portion to be engaged and positioned.

In an embodiment, a guiding mechanism is formed at two opposite ends of the liquid reserving assembly and the cigarette holder assembly for guiding the rotation of the cigarette holder assembly and limiting the cigarette holder assembly to rotating between a third position and a fourth position; when being in the third position, the cigarette holder assembly blocks the liquid inlet, and the smoke outlet communicates with the smoke passage, and when the cigarette holder assembly is in the fourth position, the liquid inlet is exposed, and the smoke outlet is staggered from the smoke passage.

In an embodiment, the rotation axis of the cigarette holder assembly is offset from the smoke passage, the rotation axis of the cigarette holder assembly and the guiding mechanism are respectively located on opposite sides of the smoke outlet.

In an embodiment, the guiding mechanisms includes a positioning protrusion and an arcuate guiding portion; the positioning protrusion is arranged on an end surface of the liquid reserving assembly corresponding to the cigarette holder assembly, and the guiding portion is formed on the cigarette holder assembly cooperating with the positioning protrusion; and an axis of the positioning protrusion coincides with the rotation axis of the cigarette holder assembly.

In an embodiment, the positioning protrusion includes a supporting platform and an engaging portion, the supporting platform projects from the liquid reserving assembly towards a side of the cigarette holder assembly, and the engaging portion is engaged with the guiding portion to prevent the cigarette holder assembly from moving away from the liquid reserving assembly; the engaging portion includes a hanging platform extending laterally from the supporting platform; and the guiding portion and the hanging platform are engaged with each other.

In an embodiment, a side surface of the guiding portion facing away from the liquid reserving assembly includes a first engaging position and a second engaging position, the first engaging position and the second engaging position are staggered from each other in an axial direction of the cigarette holder assembly, and the first engaging position is further away from the liquid reserving assembly relative to the second engaging position; when the cigarette holder assembly is in the third position, the positioning protrusion is engaged with the first engaging position, and when the cigarette holder is in the fourth position, the positioning protrusion is engaged with the second engaging position.

In an embodiment, the cigarette holder assembly includes an annular mouthpiece holder and a mouthpiece tube mounted in an annular hole of the mouthpiece holder, and the positioning member is annular and sleeved on the mouthpiece tube, cooperating with the mouthpiece holder; the guiding portion is formed on the mouthpiece holder, the positioning member covers the mouthpiece holder, the sleeve portion encloses an outer ring of the mouthpiece holder, and a rotation of the cigarette holder assembly is limited by at least one end of the mouthpiece tube on the guiding portion; and/or, the guiding portion is formed on the mouthpiece holder, and the positioning member covers the mouthpiece holder, and a rotation of the cigarette holder assembly is limited by at least one end of the mouthpiece tube on the guiding portion.

The present disclosure further provides an electronic cigarette having the above atomizing device.

In the electronic cigarette and the atomizing device thereof provided in the present disclosure, the positioning member is capable of being engaged with the liquid reserving assembly and thus being positioned, thus, when liquid injection is not required, the opening of the liquid inlet caused by the rotation of the cigarette holder assembly relative to the liquid reserving assembly by misoperation can be prevented to avoid the leakage risk of the tobacco liquid, improving the safety and health of the electronic cigarette.

BRIEF DESCRIPTION OF THE DRAWINGS

The present disclosure will be described in more detail with reference to the accompany drawings and the embodiments, wherein in the drawings.

PREFERRED EMBODIMENTS

The preferred embodiments are illustrated in detail with reference to the attached drawings so as to have a clearer understanding of the technical characteristics, purpose and effect of the present disclosure.

Figure 1:
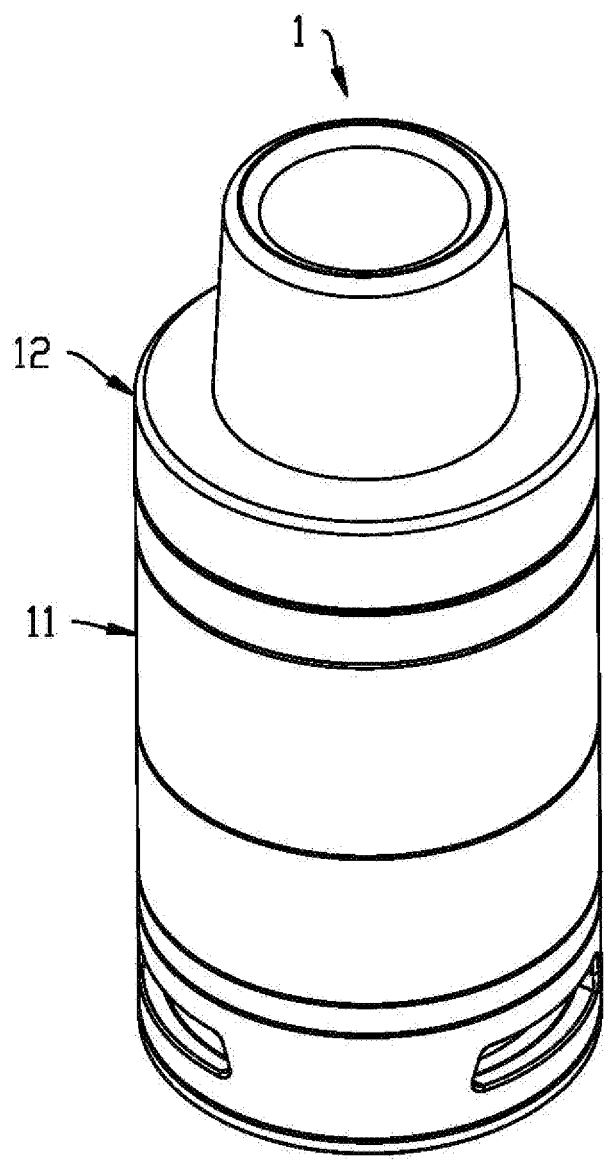
FIG. 1 is a schematic view of a cigarette holder assembly of an atomizing device in a third position in accordance with an embodiment of the present disclosure.

An electronic cigarette in an embodiment of the present disclosure is shown in FIG. 1. The electronic cigarette includes an atomizing device 1 and a power supply device. After the atomizing device 1 is assembled to the power supply device, the power supply device supplies power to the atomizing device 1 to atomize the liquid in the atomizing device 1 to be smoked by the user.

Figure 2:
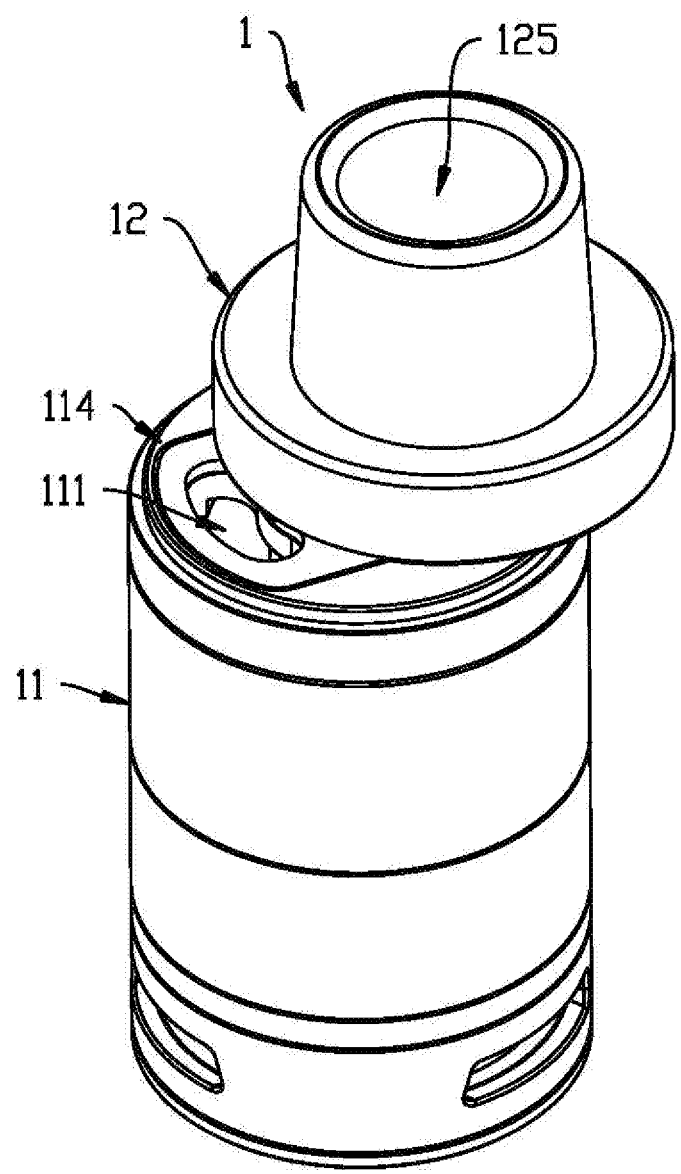
FIG. 2 is a schematic view of the cigarette holder assembly of the atomizing device of FIG. 1 in a fourth position in accordance with an embodiment of the present disclosure.
Figure 3:
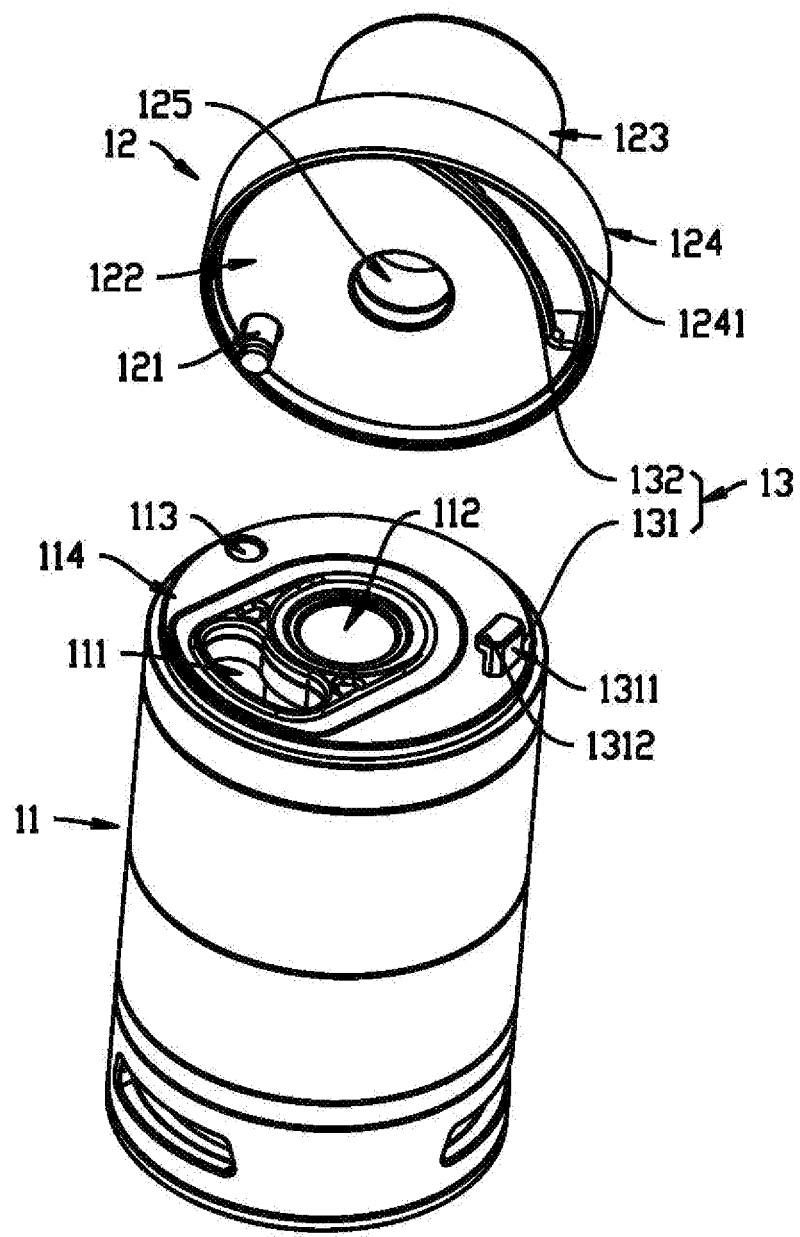
FIG. 3 is a three-dimension view of the cigarette holder assembly and a liquid reserving assembly of the atomizing device of FIG. 1 in a disassembled state in accordance with an embodiment of the present disclosure.

The atomizing device 1 in some embodiments of the present disclosure is shown from FIG. 1 to FIG. 3. The atomizing device 1 includes a liquid reserving assembly 11 and a cigarette holder assembly 12 rotatably mounted at one end of the liquid reserving assembly 11. A liquid storage cavity is formed inside the liquid reserving assembly 11. One end of the liquid reserving assembly 11 corresponding to the cigarette holder assembly 12 forms a liquid inlet 111 for injecting liquid into the liquid storage cavity, thus, tobacco liquid can be re-injected into the liquid storage cavity after the tobacco liquid is exhausted.

The cigarette holder assembly 12 has an axially-penetrating smoke outlet 125, and the liquid reserving assembly 11 includes a smoke passage 112 correspondingly communicating with the smoke outlet 125. When the user smokes the electronic cigarette, atomized tobacco liquid in the liquid reserving assembly 11 flows to the smoke outlet 125 to enter the user's mouth through the smoke passage 112.

When the electronic cigarette is in normal use, the cigarette holder assembly 12 blocks the liquid inlet 111 to prevent the tobacco liquid on the liquid inlet 111 from affecting the appearance of the electronic cigarette. Further, a rotation axis of the cigarette holder assembly 12 is offset from the liquid inlet 111 to expose the liquid inlet 111 after rotation.

Figure 4:
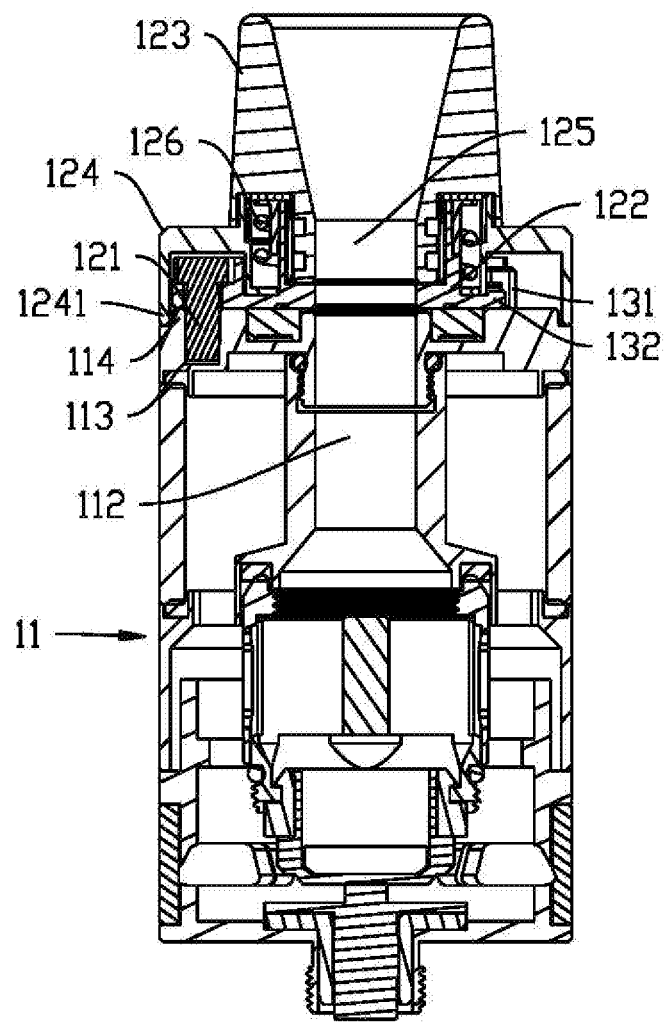
FIG. 4 is a cross-sectional view of a positioning member and a mouthpiece holder of the cigarette holder assembly of FIG. 1 in a disassembled state in accordance with an embodiment of the present disclosure.
Figure 5:
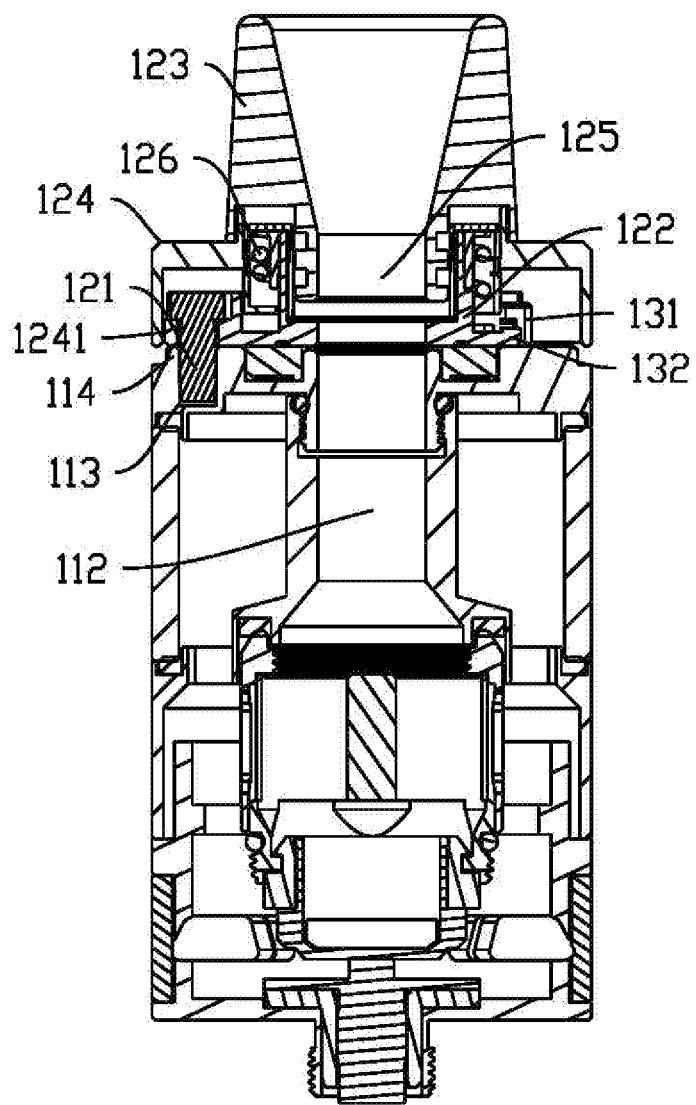
FIG. 5 is a cross-sectional view of the positioning member of FIG. 1 in a first position in accordance with an embodiment of the present disclosure.

As shown from FIG. 3 to FIG. 5, the cigarette holder assembly 12 includes a positioning member 124 axially movable between a first position and a second position. When being in the first position, the positioning member 124 engages with the liquid reserving assembly 11 to limit the cigarette holder assembly 12 to rotating relative to the liquid reserving assembly 11, and the cigarette holder assembly 12 blocks the liquid inlet 111. When being in the second position, the positioning member 124 separates from the liquid reserving assembly 11, so that the cigarette holder assembly 12 rotates relative to the liquid reserving assembly 11 to expose the liquid inlet 111.

The positioning member 124 can be engaged with the liquid reserving assembly 11 to avoid the risk of leakage of the tobacco liquid caused by the opening of the liquid inlet 22 when liquid injection is not required, which may be caused by the rotation of the cigarette holder assembly 12 relative to the liquid reserving assembly 11 by wrong operation, thereby improving the safety and health of the electronic cigarette.

The cigarette holder assembly 12 includes an elastic member 126 that provides an elastic force for holding the positioning member 124 in the first position, so that the positioning member 124 can automatically restore to the first position to be engaged with the liquid reserving assembly 11 when no external force is imposed to the positioning member 126. The elastic member 126 can be a spring or a shrapnel, etc.

The positioning member 124 includes an annular sleeve portion 1241. One end of the sleeve portion 1241 is sleeved at the end of the liquid reserving assembly 11 corresponding to the cigarette holder assembly 12.

A shape of an outer ring of the sleeve portion 1241 is equivalent to a shape of a cross section of the liquid reserving assembly 11. An annular clamping table 114 is arranged at one end of the liquid reserving assembly 11 corresponding to the sleeve portion 1241, and the clamping table 114 corresponds to a shape of an inner ring of the sleeve portion 1241 for the sleeve portion 1241 to be engaged and positioned. The clamping table 114 limits the sleeve portion 1241 and the cigarette holder assembly 12 laterally to prevent the cigarette holder assembly 12 from rotating laterally to open the liquid inlet 111.

In one embodiment, in order to prevent unstable operation such as axial movement during the rotation of the cigarette holder assembly 12, a guiding mechanism 13 is formed at two opposite ends of the liquid reserving assembly 11 and the cigarette holder assembly 12, which can guide the rotation of the cigarette holder assembly 12 and limit the cigarette holder assembly 12 to rotating between a third position and a fourth position. The guiding mechanism 13 limits the cigarette holder assembly 12 to rotating in a specific range of rotation and rotating only across an end surface of the liquid reserving assembly 11 about the rotation axis, thus, the stable connection between the cigarette holder assembly 12 and the liquid reserving assembly 11 may not be affected by the axial movement and shaking of the cigarette holder assembly 12, which may result in a gap therebetween to affect the sealing effect of the tobacco liquid.

Figure 6:
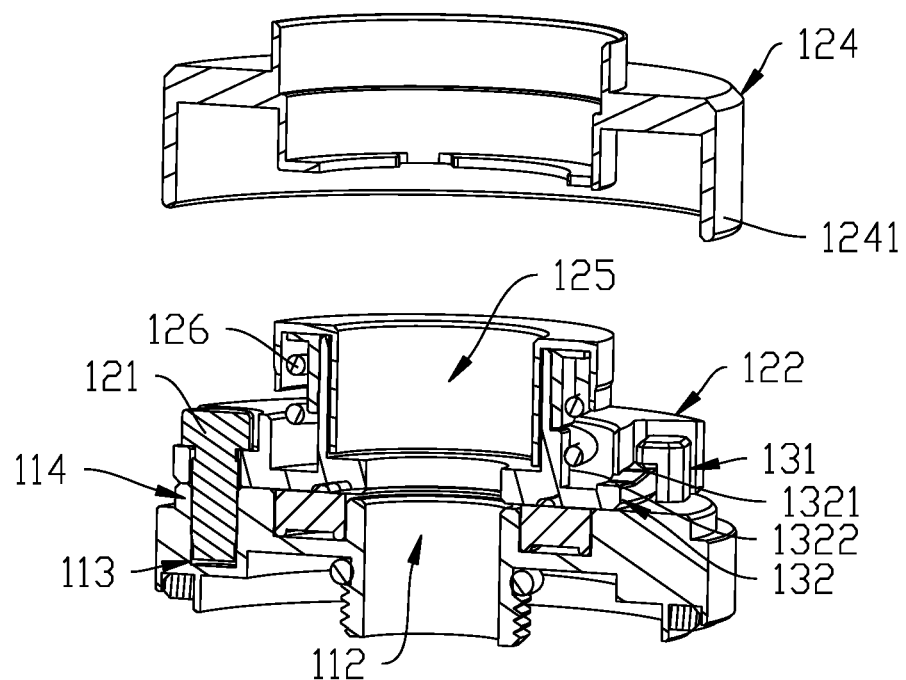
FIG. 6 is a cross-sectional view of the positioning member of FIG. 1 in a second position in accordance with an embodiment of the present disclosure.

As shown in FIG. 2, FIG. 3 and FIG. 6, in some embodiments, the cigarette holder assembly 12 has a rotating shaft 121, and the liquid reserving assembly 11 defines a shaft hole 113 for rotatably mounting the rotating shaft 121. In other embodiments, the positions of the rotating shaft 121 and the shaft hole 113 can also be reversed certainly. In one embodiment, the rotation axis of the cigarette holder assembly 12 is offset from the smoke passage 112, and the rotation axis of the cigarette holder assembly 12 and the guiding mechanism 13 are respectively located on opposite sides of the smoke outlet 125. When the cigarette holder assembly 12 is rotated, the position of the smoke outlet 125 will also be offset from the smoke passage 112, When the cigarette holder assembly 12 is in the third position, the electronic cigarette is in normal use, the cigarette holder assembly 12 blocks the liquid inlet 111 to prevent the outflow of the tobacco liquid and to prevent the tobacco liquid on the liquid inlet 111 from affecting the appearance of the electronic cigarette, and at the same time, the smoke outlet 125 communicates with the smoke passage 112.

Furthermore, the rotation axis of the cigarette holder assembly 12 is offset from the smoke outlet 125 and the liquid inlet 111 to expose the liquid inlet 111 after rotation. When the cigarette holder assembly 12 is in the fourth position, the liquid inlet 111 is exposed and the smoke outlet 125 is staggered from the smoke passage 112.

In other embodiments, when the cigarette holder assembly 12 has an eccentric structure, the rotation axis of the cigarette holder assembly 12 and the guiding mechanism 13 can also be on the same side of the smoke outlet 125. When the cigarette holder assembly 12 has a non-circular structure, the rotation axis of the cigarette holder assembly 12 may be the axis of the smoke outlet 125, such that the cigarette holder assembly 12 rotates around the smoke outlet 125 to expose the liquid inlet 111 to facilitate liquid injection after the rotation.

In some embodiments, the guiding mechanism 13 includes a positioning protrusion 131 arranged on an end surface of the liquid reserving assembly 11 corresponding to the cigarette holder assembly 12, and an arcuate guiding portion 132 formed on the cigarette holder assembly 12 cooperating with the positioning protrusion 131. An axis of the guiding portion 132 coincides with the rotation axis of the cigarette holder assembly 12, so that the cigarette holder assembly 12 rotates about the rotation axis smoothly. In other embodiments, the positions of the positioning protrusion 131 and the guiding portion 132 may also be reversed.

Furthermore, in order to completely fix the cigarette holder assembly 12 in the axial direction, the positioning protrusion 131 includes a supporting platform 1311 and an engaging portion. The supporting platform 1311 projects from the liquid reserving assembly 11 towards one side of the cigarette holder assembly 12. The engaging portion is engaged with the guiding portion 132 to prevent the cigarette holder assembly 12 from moving away from the liquid reserving assembly 11, so that the cigarette holder assembly 12 rotates only about the rotation axis.

The engaging portion includes a hanging platform 1312 extending laterally from the supporting platform 1311. The guiding portion 132 and the hanging platform 1331 are engaged with each other to prevent the axial deviation of the cigarette holder assembly 12 while the cigarette holder assembly 12 is rotating.

In some embodiments, a cross section of the positioning protrusion 131 is invertedly L-shaped. In other embodiments, the cross section of the positioning protrusion 131 may be T-shaped. In addition, if the axial deviation of the cigarette holder assembly 12 while rotating can be avoided after the positioning protrusion 131 is engaged with the guiding portion 132, the shapes of the cross sections of the positioning protrusion 131 and the guiding portion 132 are not limited to this embodiment.

A side surface of the guiding portion 132 facing away from the liquid reserving assembly 11 includes a first engaging position 1321 and a second engaging position 1322. The first engaging position 1321 and the second engaging position 1322 are staggered from each other in an axial direction of the cigarette holder assembly 12, and the first engaging position 1321 is further away from the liquid reserving assembly 11 relative to the second engaging position 1322.

When the cigarette holder assembly 12 is in the third position, the positioning protrusion 131 is engaged with the first engaging position 1321; and when the cigarette holder assembly 12 is in the fourth position, the positioning protrusion 131 is engaged with the second engaging position 1322.

In other embodiments, the cigarette holder assembly 12 includes an annular mouthpiece holder 122 and a mouthpiece tube 123 mounted in an annular hole of the mouthpiece holder 122. The positioning member 124 is annular and sleeved on the mouthpiece tube 123 to be cooperated with the mouthpiece holder 122. An inner hole of the mouthpiece tube 123 forms the smoke outlet 125.

The guiding portion 132 is formed on the mouthpiece holder 122, protruding outwards from the side of the mouthpiece holder 122. The positioning member 124 is covered on the mouthpiece holder 122. The sleeve portion 1241 encloses an outer ring of the mouthpiece holder 122. The rotation of the cigarette holder assembly 12 is limited by one end of the sleeve portion 1241 on the guiding portion 132, and the other end of the guiding portion 132 is limited by the mouthpiece tube 123.

In other embodiments, the rotation of the cigarette holder assembly 12 can be limited by two ends of the sleeve portion 1241 on the guiding portion 132, or, the rotation of the cigarette holder assembly 12 can be limited by two ends of the mouthpiece tube 123 on the guiding portion 132.

A side surface of the guiding portion 132 facing away from the liquid reserving assembly 11 includes a first engaging position 1321 and a second engaging position 1322. The first engaging position 1321 and the second engaging position 1322 are staggered from each other in axial direction of the cigarette holder assembly 12, and the first engaging position 1321 is further away from the liquid reserving assembly 11 relative to the second engaging position 1322.

When the cigarette holder assembly 12 is in the third position, the positioning protrusion 131 is engaged with the first engaging position 1321, and the cigarette holder assembly 12 and the liquid reserving assembly 11 can be kept clamped to each other. When the cigarette holder assembly 12 is in the fourth position, the positioning protrusion 131 is engaged with the second engaging position 1322, as the first engaging position 1321 and the second engaging position 1322 are offset from each other in the axial direction of the electronic cigarette, the cigarette holder assembly 12 can be facilitated to rotate to the fourth position from the third position.

It can be understood that the above features can be combined in any way without limitation.

What mentioned above are only the embodiments of the present disclosure, which are not to limit the scope of the patent of the present disclosure. Any equivalent structure or equivalent transformation of the procedure made with the specification and the pictures attached of the present disclosure, or directly or indirectly using the specification and the pictures attached of the present disclosure into other relevant technical fields, is included in the scope of the patent protection of the present disclosure.

What is claimed is:

1. An atomizing device, comprising: a liquid reserving assembly (11) and a cigarette holder assembly (12) rotatably mounted at one end of the liquid reserving assembly (11);
wherein a liquid storage cavity is formed inside the liquid reserving assembly (11), and a liquid inlet (111) for injecting liquid into the liquid storage cavity is arranged at one end of the liquid reserving assembly (11) corresponding to the cigarette holder assembly (12);
the cigarette holder assembly (12) comprises an axially-penetrating smoke outlet (125), the liquid reserving assembly (11) comprises a smoke passage (112) correspondingly communicating with the smoke outlet (125), and the cigarette holder assembly (12) blocks the liquid inlet (111);
a rotation axis of the cigarette holder assembly (12) is offset from the liquid inlet (111) to expose the liquid inlet (111) after rotation;
the cigarette holder assembly (12) comprises a positioning member (124) axially movable between a first position and a second position; when being in the first position, the positioning member (124) is engaged with the liquid reserving assembly (11) to limit the cigarette holder assembly (12) to rotating relative to the liquid reserving assembly (11), and the cigarette holder assembly (12) blocks the liquid inlet (111); and when being in the second position, the positioning member (124) is separated from the liquid reserving assembly (11), so that the cigarette holder assembly (12) rotates relative to the liquid reserving assembly (11) to expose the liquid inlet (111).

2. The atomizing device of claim 1, wherein the cigarette holder assembly (12) further comprises an elastic member (126) that provides an elastic force for holding the positioning member (124) in the first position.

3. The atomizing device of claim 1, wherein the positioning member (124) comprises an annular sleeve portion (1241), one end of the sleeve portion (1241) is sleeved at the end of the liquid reserving assembly (11) corresponding to the cigarette holder assembly (12); and an annular clamping table (114) corresponding to a shape of an inner ring of the sleeve portion (1241) is arranged at one end of the liquid reserving assembly (11) corresponding to the sleeve portion (1241) for the sleeve portion (1241) to be engaged and positioned.

4. The atomizing device of claim 2, wherein a guiding mechanism (13) is formed at two opposite ends of the liquid reserving assembly (11) and the cigarette holder assembly (12) for guiding the rotation of the cigarette holder assembly (12) and limiting the cigarette holder assembly (12) to rotating between a third position and a fourth position; when being in the third position, the cigarette holder assembly (12) blocks the liquid inlet (111), and the smoke outlet (125) communicates with the smoke passage (112); and when the cigarette holder assembly (12) is in the fourth position, the liquid inlet (111) is exposed, and the smoke outlet (125) is staggered from the smoke passage (112).

5. The atomizing device of claim 4, wherein the rotation axis of the cigarette holder assembly (12) is offset from the smoke passage (112), and the rotation axis of the cigarette holder assembly (12) and the guiding mechanism (13) are respectively located on opposite sides of the smoke outlet (125).

6. The atomizing device of claim 4, wherein the guiding mechanism (13) comprises a positioning protrusion (131) and an arcuate guiding portion (132); the positioning protrusion (131) is arranged on an end surface of the liquid reserving assembly (11) corresponding to the cigarette holder assembly (12), and the guiding portion (132) is formed on the cigarette holder assembly (12) cooperating with the positioning protrusion (131); and an axis of the positioning protrusion (131) coincides with the rotation axis of the cigarette holder assembly (12).

7. The atomizing device of claim 6, wherein the positioning protrusion (131) comprises a supporting platform (1311) and an engaging portion; the supporting platform (1311) projects from the liquid reserving (11) assembly towards a side of the cigarette holder assembly (12), and the engaging portion is engaged with the guiding portion (132) to prevent the cigarette holder assembly (12) from moving away from the liquid reserving assembly (11); the engaging portion comprises a hanging platform (1312) extending laterally from the supporting platform (1311), and the guiding portion (132) and the hanging platform (1312) are engaged with each other.

8. The atomizing device of claim 6, wherein a side surface of the guiding portion (132) facing away from the liquid reserving assembly (11) comprises a first engaging position (1321) and a second engaging position (1322), the first engaging position (1321) and the second engaging position (1322) are staggered from each other in an axial direction of the cigarette holder assembly (12), and the first engaging position (1321) is further away from the liquid reserving assembly (11) relative to the second engaging position (1322); when the cigarette holder assembly (12) is in the third position, the positioning protrusion (131) is engaged with the first engaging position (1321), and when the cigarette holder assembly (12) is in the fourth position, the positioning protrusion (131) is engaged with the second engaging position (1322).

9. The atomizing device of claim 4, wherein the cigarette holder assembly (12) comprises an annular mouthpiece holder (122) and a mouthpiece tube (123) mounted in an annular hole of the mouthpiece holder (122), and the positioning member (124) is annular and sleeved on the mouthpiece tube (123), cooperating with the mouthpiece holder (122);
the guiding portion (132) is formed on the mouthpiece holder (122), the positioning member (124) covers the mouthpiece holder (122), the sleeve portion (1241) encloses an outer ring of the mouthpiece holder (122), and a rotation of the cigarette holder assembly (12) is limited by at least one end of the mouthpiece tube (123) on the guiding portion (132).

10. An electronic cigarette, comprising an atomizing device (1), wherein the atomizing device (1) comprises a liquid reserving assembly (11) and a cigarette holder assembly (12) rotatably mounted at one end of the liquid reserving assembly (11);
wherein a liquid storage cavity is formed inside the liquid reserving assembly (11), and a liquid inlet (111) for injecting liquid into the liquid storage cavity is arranged at one end of the liquid reserving assembly (11) corresponding to the cigarette holder assembly (12);
the cigarette holder assembly (12) comprises an axially-penetrating smoke outlet (125), the liquid reserving assembly (11) comprises a smoke passage (112) correspondingly communicating with the smoke outlet (125), and the cigarette holder assembly (12) blocks the liquid inlet (111);

a rotation axis of the cigarette holder assembly (12) is offset from the liquid inlet (111) to expose the liquid inlet (111) after rotation;

the cigarette holder assembly (12) comprises a positioning member (124) axially movable between a first position and a second position; when being in the first position, the positioning member (124) is engaged with the liquid reserving assembly (11) to limit the cigarette holder assembly (12) to rotating relative to the liquid reserving assembly (11), and the cigarette holder assembly (12) blocks the liquid inlet (111); and when being in the second position, the positioning member (124) is separated from the liquid reserving assembly (11), so that the cigarette holder assembly (12) rotates relative to the liquid reserving assembly (11) to expose the liquid inlet (111).

11. The electronic cigarette of claim 10, wherein the cigarette holder assembly (12) further comprises an elastic member (126) that provides an elastic force for holding the positioning member (124) in the first position.

12. The electronic cigarette of claim 10, wherein the positioning member (124) comprises an annular sleeve portion (1241), one end of the sleeve portion (1241) is sleeved at the end of the liquid reserving assembly (11) corresponding to the cigarette holder assembly (12); and an annular clamping table (114) corresponding to a shape of an inner ring of the sleeve portion (1241) is arranged at one end of the liquid reserving assembly (11) corresponding to the sleeve portion (1241) for the sleeve portion (1241) to be engaged and positioned.

13. The electronic cigarette of claim 11, wherein a guiding mechanism (13) is formed at two opposite ends of the liquid reserving assembly (11) and the cigarette holder assembly (12) for guiding the rotation of the cigarette holder assembly (12) and limiting the cigarette holder assembly (12) to rotating between a third position and a fourth position; when being in the third position, the cigarette holder assembly (12) blocks the liquid inlet (111), and the smoke outlet (125) communicates with the smoke passage (112); and when the cigarette holder assembly (12) is in the fourth position, the liquid inlet (111) is exposed, and the smoke outlet (125) is staggered from the smoke passage (112).

14. The electronic cigarette of claim 13, wherein the rotation axis of the cigarette holder assembly (12) is offset from the smoke passage (112), and the rotation axis of the cigarette holder assembly (12) and the guiding mechanism (13) are respectively located on opposite sides of the smoke outlet (125).

15. The electronic cigarette of claim 13, wherein the guiding mechanism (13) comprises a positioning protrusion (131) and an arcuate guiding portion (132); the positioning protrusion (131) is arranged on an end surface of the liquid reserving assembly (11) corresponding to the cigarette holder assembly (12), and the guiding portion (132) is formed on the cigarette holder assembly (12) cooperating with the positioning protrusion (131); and an axis of the positioning protrusion (131) coincides with the rotation axis of the cigarette holder assembly (12).

16. The electronic cigarette of claim 15, wherein the positioning protrusion (131) comprises a supporting platform (1311) and an engaging portion; the supporting platform (1311) projects from the liquid reserving (11) assembly towards a side of the cigarette holder assembly (12), and the engaging portion is engaged with the guiding portion (132) to prevent the cigarette holder assembly (12) from moving away from the liquid reserving assembly (11); the engaging portion comprises a hanging platform (1312) extending laterally from the supporting platform (1311), and the guiding portion (132) and the hanging platform (1312) are engaged with each other.

17. The electronic cigarette of claim 15, wherein a side surface of the guiding portion (132) facing away from the liquid reserving assembly (11) comprises a first engaging position (1321) and a second engaging position (1322), the first engaging position (1321) and the second engaging position are staggered from each other in an axial direction of the cigarette holder assembly (12), and the first engaging position (1321) is further away from the liquid reserving assembly (11) relative to the second engaging position (1322); when the cigarette holder assembly (12) is in the third position, the positioning protrusion (131) is engaged with the first engaging position (1321), and when the cigarette holder assembly (12) is in the fourth position, the positioning protrusion (131) is engaged with the second engaging position (1322).

18. The electronic cigarette of claim 13, wherein the cigarette holder assembly (12) comprises an annular mouthpiece holder (122) and a mouthpiece tube (123) mounted in an annular hole of the mouthpiece holder (122), and the positioning member (124) is annular and sleeved on the mouthpiece tube (123), cooperating with the mouthpiece holder (122); and the guiding portion (132) is formed on the mouthpiece holder (122), the positioning member (124) covers the mouthpiece holder (122), the sleeve portion (1241) encloses an outer ring of the mouthpiece holder (122), and a rotation of the cigarette holder assembly (12) is limited by at least one end of the mouthpiece tube (123) on the guiding portion (132).

19. The electronic cigarette of claim 13, wherein the cigarette holder assembly (12) comprises an annular mouthpiece holder (122) and a mouthpiece tube (123) mounted in an annular hole of the mouthpiece holder (122), and the positioning member (124) is annular and sleeved on the mouthpiece tube (123), cooperating with the mouthpiece holder (122); and the guiding portion (132) is formed on the mouthpiece holder (122), and the positioning member (124) covers the mouthpiece holder (122), and a rotation of the cigarette holder assembly (12) is limited by at least one end of the mouthpiece tube (123) on the guiding portion (132).

20. The atomizing device of claim 4, wherein the cigarette holder assembly (12) comprises an annular mouthpiece holder (122) and a mouthpiece tube (123) mounted in an annular hole of the mouthpiece holder (122), and the positioning member (124) is annular and sleeved on the mouthpiece tube (123), cooperating with the mouthpiece holder (122);

the guiding portion (132) is formed on the mouthpiece holder (122), and the positioning member (124) covers the mouthpiece holder (122), and a rotation of the cigarette holder assembly (12) is limited by at least one end of the mouthpiece tube (123) on the guiding portion (132).

* * * * *